United States Patent [19]

Yoshioka et al.

[11] Patent Number: 4,659,739
[45] Date of Patent: Apr. 21, 1987

[54] AGRICULTURAL AND HORTICULTURAL GUANIDINE-TYPE FUNGICIDE AND PROCESS FOR PRODUCTION THEREOF

[75] Inventors: Nobuyuki Yoshioka; Yasuji Okunishi; Yasuhisa Miura, all of Hasaki; Yoshikazu Mori, Sahara; Yasuki Kataoka, Shisui; Eiichi Adachi, Yokohama, all of Japan

[73] Assignee: Dainippon Ink and Chemicals, Inc., Tokyo, Japan

[21] Appl. No.: 705,365

[22] Filed: Feb. 25, 1985

[30] Foreign Application Priority Data

Feb. 24, 1984 [JP] Japan .................................. 59-33978

[51] Int. Cl.⁴ .................. C07C 129/16; C07C 133/10; A01N 33/04
[52] U.S. Cl. ................. 514/555; 260/501.14; 514/554
[58] Field of Search ................ 260/501.14; 514/554, 514/555

[56] References Cited

U.S. PATENT DOCUMENTS

| | | | |
|---|---|---|---|
| 1,915,922 | 6/1933 | Christmann et al. | 514/555 |
| 2,409,883 | 10/1946 | Migrdichian | 514/554 |
| 2,473,112 | 6/1949 | Short et al. | 260/501.14 |
| 2,702,819 | 2/1955 | Axe et al. | 260/501.14 |
| 2,823,182 | 2/1958 | McLoed et al. | 260/501.14 |
| 2,832,743 | 4/1958 | Libby et al. | 260/501.14 |
| 2,867,562 | 1/1959 | Lamb | 260/501.14 |
| 2,906,595 | 9/1959 | Pelcak et al. | 514/554 |
| 3,067,090 | 12/1962 | Bel | 260/501.14 |
| 3,142,615 | 7/1964 | Wehner | 260/501.14 |
| 3,174,978 | 3/1965 | Marxer | 260/501.14 |
| 3,272,693 | 9/1966 | Harrison | 514/554 |
| 3,468,898 | 9/1969 | Cutler et al. | 260/501.14 |
| 3,639,631 | 2/1972 | Badcock et al. | 514/636 |
| 4,053,636 | 10/1977 | Eustis et al. | 260/501.14 |
| 4,080,472 | 3/1978 | Bohuon | 260/501.14 |
| 4,092,432 | 5/1978 | Bjorklund et al. | 260/501.14 |
| 4,139,555 | 2/1979 | Zerbes | 260/501.14 |
| 4,149,980 | 4/1979 | Abdul-Malek et al. | 260/501.14 |

FOREIGN PATENT DOCUMENTS

| | | | |
|---|---|---|---|
| 2037002 | 12/1970 | France | 260/501.14 |
| 2110209 | 6/1983 | United Kingdom | 514/555 |

*Primary Examiner*—J. E. Evans
*Attorney, Agent, or Firm*—Sherman and Shalloway

[57] ABSTRACT

An agricultural and horticultural fungicide of low phytotoxicity comprising as an active ingredient an addition salt between a fungicidal guanidine compound and an acid having an oleophilic group with at least 9 carbon atoms in total. The acid addition salt is produced by reacting a fungicidal guanidine compound or its acid addition salt with an acid having an oleophilic group with at least 9 carbon atoms in total or its salt.

8 Claims, No Drawings

AGRICULTURAL AND HORTICULTURAL GUANIDINE-TYPE FUNGICIDE AND PROCESS FOR PRODUCTION THEREOF

This invention relates to an agricultural and horticultural guanidine-type fungicide of reduced phytotoxicity to useful plants which comprises as an active ingredient a water-insoluble acid addition salt of a fungicidal guanidine compound obtained by reacting the fungicidal guanidine compound with an acid having an oleophilic group with at least 9 carbon atoms in total such as an alkylbenzenesulfonic acid.

One specific example of the fungicidal guanidine compound is 1,1'-iminodi(octamethylene)-diguanidinium triacetate (to be referred to as the guazatine acetate). This compound is known, however, to cause strong phytotoxicity to some types of agricultural crops. Generally, the strong phytotoxicity of many fungicidal guanidine compounds to useful plants has precluded their practical application as agricultural and horticultural fungicides or limited the range of their application as such despite their significant efficacy as an active ingredient of such fungicides.

For example, guazatine is known to be effective on a broad range of diseases occurring in useful plants (see, for example, U. S. Pat. Nos. 3,499,927 and 3,639,631). It is generally applied as a low-molecular-weight acid addition salt, for example as a mineral acid salt such as a hydrochloride, sulfate, carbonate, nitrate or phosphate, or as an organic acid salt such as a formate, acetate, lactate, succinate, maleate, citrate, salicylate or p-toluenesulfonate. Guazatine in the form of such an addition salt shows an excellent control effect on diseases occurring in useful plants, but causes considerable phytotoxicity to the leaves, stalks, fruits, tree stems, etc. of many plants in the growing period. This phytotoxicity constitutes a setback in its practical application and therefore the range of its application has frequently been restricted.

It is therefore an object of this invention to provide a fungicide which has a control effect on many plant diseases comparable to that possessed by guazatine and yet can avoid phytotoxicity to useful plants.

The object of this invention is achieved by an agricultural and horticultural guanidine-type fungicide having reduced phytotoxicity to useful plants, comprising as an active ingredient an addition salt between a fungicidal guanidine compound and an acid having an oleophilic group with at least 9 carbon atoms in total, particularly an addition salt of the fungicidal guanidine compound with a carboxylic acid, sulfuric acid monoester, sulfonic acid or phosphoric acid ester having an oleophilic group with at least 9 carbon atoms in total.

The reduction in the phytotoxicity of fungicidal guanidine compounds achieved by the present invention has now enabled the fungicidal guanidine compounds to be applied to scab (*Venturia inaequalis*) of apple, brown rot (*Sclerotinia cinerea*) of peach, black spot (*Alternaria kikuchiana*) and scab (*Venturia nashicola*) of pear, gray mold (*Botrytis cinerea*) of grape, powdery mildew (*Sphaerotheca fuliginea*) and gray mold (*Botrytis cinerea*) of cucumber, and anthracnose (*Colletotrichum lagenarium*) of watermelon to which these guanidine compounds have previously been unable to be applied in practical concentrations because of their strong phytotoxicity. The present invention has also made it possible to apply the fungicidal guanidine compounds to diseases of many useful plants including peach, chestnut, persimmon, grape, citruses (such as orange, lemon and grape fruit), cucumber, eggplant, green pepper, onion, potato, radish, melon, watermelon, rose and cyclamen.

Examples of the fungicidal guanidine compounds in this invention include 1,1'-iminodi(octamethylene)-diguanidine (common name: guazatine) of the following formula

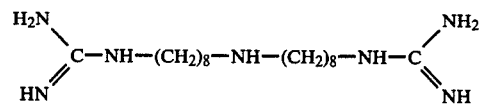

1,8-diguanidinooctane and 1,12-diguanidinododecane (Japanese Laid-Open Patent Publication No. 48902/1982); bis(8-guanidinooctyl) ether, bis(8-guanidinooctyl) thioether and 8-guanidinooctyl-3-guanidinopropyl ether (Japanese Laid-Open Patent Publication No. 95102/1981); and aliphatic polyamines having a guanidino group introduced thereinto (U.S. Pat. No. 4,092,432) such as $G(CH_2)_8G(CH_2)_8NH(CH_2)_8$, $H_2N(CH_2)_8G(CH_2)_8NH_2$, $G(CH_2)_8G(CH_2)_8NH_2$, $G(CH_2)_8G(CH_2)_8G$, $G(CH_2)_8NH(CH_2)_8G$, $G(CH_2)_8G(CH_2)_8G(CH_2)_8G$, $G(CH_2)_8NH(CH_2)_8G(CH_2)_8G$, and $G(CH_2)_8NH(CH_2)_8NH(CH_2)_8NH_2$ (wherein G represents a guanidino group).

The acid forming the acid addition salt in accordance with this invention has an oleophilic group having at least 9 carbon atoms in total, preferably one in which the oleophilic group is a linear, branched or cyclic alkyl or alkylaryl group having at least 9 carbon atoms in total, especially preferably a carboxylic acid, sulfuric acid monoester, sulfonic acid or phosphoric acid ester having an oleophilic group with at least 9 carbon atoms, preferably 9 to 25 carbon atoms, especially preferably 11 to 20 carbon atoms, in total.

The carboxylic acid in this invention may be one having an oleophilic group with at least 9, preferably 9 to 25, carbon atoms in total, for example saturated or unsaturated fatty acids, carboxylic acids having a linear, branched or cyclic alkyl group, and carboxylic acids having the aforesaid alkyl group substituted by another functional group such as $-SO_3H$, $-OH$, $-SH$ or $-NO_2$.

Examples of such carboxylic acids include capric acid, lauric acid, myristic acid, palmitic acid, stearic acid, arachidic acid, behenic acid, oleic acid, erucic acid, linoleic acid, linolenic acid, eleostearic acid, sulfonated fatty acids, hydroxyl-containing fatty acids, cyclic fatty acids, dimeric acids and mixtures of two or more of these. Examples of the mixtures of such carboxylic acids are higher fatty acids obtained from animal and vegetable oils such as lard, sheep tallow, beef tallow, butter fat, coconut oil, soybean oil, olive oil, castor oil, palm oil, sesame oil, bran oil, tall oil, cottonseed oil, poppyseed oil, linseed oil, perilla oil, tung oil, rapeseed oil and peanut oil. Resin acids such as abietic acid, neoabietic acid and dehydroabietic acid and carboxylic acids having a polycyclic oleophilic group such as naphthenic acid can also be cited as examples.

The sulfuric acid monoester is a sulfuric acid monoester comprising an oleophilic group having at least 9, preferably 9 to 25, carbon atoms in total. Examples include monoesters of sulfuric acid with primary higher alcohols, monoesters of sulfuric acid with secondary higher alcohols, sulfuric acid monoesters of higher fatty acid esters, monoesters of sulfuric acid with higher alcohol ethers, monoesters of alkylolated sulfuric acid with higher fatty acid amides, and mixtures of two or more of these.

The sulfonic acid is a sulfonic acid comprising an oleophilic group containing at least 9, preferably 9 to 25, especially preferably 11 to 20, carbon atoms. Examples include primary higher alkylsulfonic acids, secondary higher alkylsulfonic acids, sulfonic acid of the aforesaid higher fatty acid esters, sulfonic acids of higher alcohol ethers, alkylsulfonic acids of higher fatty acid amides, sulfosuccinic acid esters, alkylbenzenesulfonic acids in which the alkyl moiety has 8 to 14 carbon atoms, alkylphenolsulfonic acids, alkylnaphthalenesulfonic acids, alkyldiphenylsulfonic acids, alkylaryl ether sulfonic acids, alkylaryl ester sulfonic acids, alkylaryl ketone sulfonic acids, alkylbenzimidazolesulfonic acids, ligninsulfonic acid and mixtures of two or more of these. The alkylbenzenesulfonic acids are especially preferred.

The phosphoric acid ester is a phosphoric monoor di-ester having an oleophilic group with at least 9, preferably 9 to 25, carbon atoms. Examples include esters of phosphoric acid with linear higher alcohols such as dodecyl phosphate or oleyl phosphate, esters of phosphoric acid with branched higher alcohols such as (2-ethylhexyl) phosphate, esters of phosphoric acid with alkylphenols such as di(p-nonylphenyl) phosphate, and alkylphenol ethylene oxide adduct esters of phosphoric acid such as di(polyethylene glycol p-nonylphenyl) phosphate.

In the production of the acid addition salt in accordance with this invention, the aforesaid carboxylic acids, sulfonic acids, sulfuric acid monoesters and phosphoric acid esters may be used in the form of free acids or salts with alkaline substances. Examples of the alkaline substances used in this case include amines such as ammonia, monoethanolamine, diethanolamine, triethanolamine and ethylenediamine, alkali metals such as sodium and potassium, and alkaline earth metals such as calcium.

The useful plants to which the present invention is applicable include all plants cultivated in agriculture and horticulture, and include, for example, fruit trees such as peach, pear, chestnut, citruses (orange, lemon and grape fruit), grape, apple, persimmon, plum, banana and pineapple; ornamental flowers such as cyclamen, chrysanthemum, rose, tulip and orchid; vegetables such as garland, Chinese cabbage, radish, burdock, green pepper, onion, potato, cucumber, eggplant, watermelon, melon, strawberry, tomato, lettuce, celery, cabbage, beet and sugarcane; cereals such as rice, wheat, barley, corn and Chinese sorghum; beans such as soybean; turf grasses; forage grasses; and other cultivated plants such as rape, tobacco, pepper, coffee, cotton, and sunflower.

The fungicide of this invention is applied to plants or soil by various known methods such as spraying, pouring or coating. When it is to be used by spraying, the concentration of the active ingredient in the spray liquid is usually 50 to 5000 ppm, preferably 100 to 1000 ppm, and the fungicide is used after diluting it to 10 to 5000 times, preferably 100 to 2000 times. When the fungicide of the invention is poured into, or mixed with, the soil in order to control fungi in the soil, it is preferably used as a dust or a diluted liquid so that the rate of application of the active ingredient becomes 1 to 5 g/m$^2$ of soil.

The active ingredient of the fungicide of this invention can be obtained by mixing an addition salt of the fungicidal guanidine compound with an acid having no oleophilic group or an acid having an oleophilic group with less than 9 carbon atoms in total (to be referred to as an acid addition salt) with the above-described acid having an oleophilic group with at least 9 carbon atoms in total or its alkali salt to perform salt exchanging reaction. Examples of the acid having no oleophilic group or having an oleophilic group with less than 9 carbon atoms in total include mineral acids such as hydrochloric acid, sulfuric acid, carbonic acid, nitric acid and phosphoric acid and organic acids such as formic acid, acetic acid, oxalic acid, lactic acid, succinic acid, maleic acid, citric acid, salicylic acid and p-toluenesulfonic acid. The mineral acids are preferred. Carbonic acid is especially preferred because it can be removed as a gas after the salt exchanging reaction, and the manufacturing operation is easy. As required, the original acid formed as a by-product of the salt exchanging reaction may be separated and removed.

Specifically, in the production of the fungicide of this invention, the fungicidal guanidine compound or its acid addition salt is dissolved or suspended in a solvent, and the acid is added with stirring at a temperature of 0° to 120° C., preferably 20° to 80° C., in the presence, as required, of a catalyst. The mixture is aged for 0.5 to 2 hours to perform the salt exchanging reaction. The equivalent ratio of the fungicidal guanidine compound or its acid addition salt (A) to the acid (B) in this reaction is from 1:1–4, preferably about 1:1. If the equivalent ratio of (A) to (B) is 1: less than 1, the extent of reducing the phytotoxicity of the fungicidal guanidine compound is small, and the resulting product does not have practical utility. If the equivalent ratio is 1:more than 4, the extent of reducing the phytotoxicity remains unchanged from that achieved when the equivalent ratio is 1:4, and this is economically wasteful.

The solvent used in the reaction may be any solvent capable of dissolving the acid addition salt obtained in this invention. Illustrative of the solvent are alcohols such as methanol and isopropanol, toluene, dimethyl sulfoxide and dimethylformamide.

The active ingredient of the fungicide of this invention may also be produced by subjecting the acid addition salt of the guanidine compound to ion exchange by an ion exchange resin, and reacting the resulting free base of the guanidine compound with the aforesaid acid having an oleophilic group with at least 9 carbon atoms. The invention also embraces a process which comprises mixing the aforesaid conventionally used acid addition salt with the aforesaid acid or its alkali salt, formulating the mixture into a preparation, and dissolving the preparation in water to thereby form the fungicide of the invention immediately before application. In this process, the theoretical equivalent ratio of the acid addition salt (A) to the acid or its alkali salt (B) is 1:1–4, preferably 1:1.0–1.5. The alkali salt of the acid is preferably an alkali salt of a sulfonic acid having an oleophilic group with at least 9 carbon atoms, especially preferably an alkali salt of an alkylarylsulfonic acid.

The fungicide of this invention can also be produced immediately before application by mixing an aqueous solution of the aforesaid conventionally used acid addition salt with the aforesaid acid having an oleophilic group with at least 9 carbon atoms or its alkali salt prepared separately, and thereby performing salt exchanging reaction. The mixing ratio in this case is the same as in the case of forming the formulated preparation described above.

Examples of the active ingredient of the fungicide of this invention obtained by the above methods are summarized in Table 1.

TABLE 1

| Compound No. | Compound |
| --- | --- |
| 1 | Guazatine trilaurate |
| 2 | Guazatine trimyristate |
| 3 | Guazatine tripalmitate |
| 4 | Guazatine tristearate |
| 5 | Guazatine trioleate |
| 6 | Guazatine trilinolate |
| 7 | Guazatine triabietate |
| 8 | Guazatine tri-tall oil fatty acid (Hartall SR-30*) salt |
| 9 | Guazatine trilalurylsulfate |
| 10 | Guazatine tritetradecylsulfate |
| 11 | Guazatine trihexadecylsulfate |
| 12 | Guazatine tristearylsulfate |
| 13 | Guazatine tridodecylbenzenesulfonate |
| 14 | Guazatine tritridecylbenzenesulfonate |
| 15 | Guazatine triphenylstearatesulfonate |
| 16 | Guazatine trilaurylbenzyl ether sulfonate |
| 17 | Guazatine triphenylundecyl ketone sulfonate |
| 18 | Guazatine trilaurate benzylamidosulfonate |
| 19 | Guazatine di(2-ethylhexyl) triphosphate salt |

*a trade name for a product of Harima Chemical Industry Co., Ltd.

The agricultural and horticultural guanidinetype fungicide of this invention can be used in various forms, for example as a wettable powder, dust, emulsifiable concentrate, oil, suspension, paste, etc. in admixture of suitable carriers according to the purpose of application.

The carrier may be a solid or liquid carrier. Example of the solid carrier are clay, talc, diatomaceous earth, silica (white carbon), calcium carbonate, sodium carbonate, sodium sulfate, urea, ammonium sulfate, glucose and starch. Examples of the liquid carrier include water, alcohols, glycols, dimethylformamide, dimethyl sulfoxide, animal oils and surface-active agents.

The effect of the agricultural and horticultural fungicide of this invention can be ensured by using it with adjuvants usually employed in agricultural chemicals, such as spreaders, emulsifiers, wetting agents, dispersing agents and stickers mixed properly by a customary method. The fungicide of this invention can also be used as an admixture with at least one other agricultural chemical, for example insecticides such as malathion, fenvalerate, diazinon, salithion, chlorpyrifos, methomyl, MEP (Fenitrothion) and DDVP (Dichlorvos); acaricides such as amitraz, petroleum oil, chloropropylate and dicofol; other fungicides such as TPN (Chlorothalonil), fthalide, captan, thiophanatemethyl, benomyl, oxine-copper, polyoxins, iprodione, vinclozoline, procymidone and mepronil; plant growth regulators; and fertilizers.

The following examples illustrate the present invention in greater detail. All parts and percentages in these examples are by weight, and the types and mixing proportions of the additives are not limited to those shown in these examples.

EXAMPLE 1

Wettable powder:

Guazatine sesquicarbonate (8.4 parts) was dissolved in 150 parts of methanol at 50° C., and with stirring, 11.2 parts of lauric acid was added. Methanol was evaporated under reduced pressure to give 17.9 parts of guazatine trilaurate (compound No. 1).

Guazatine trilaurate (17.9 parts), 30 parts of white carbon, 5 parts of polyoxyethylene nonylphenyl ether and 47.1 parts of finely divided clay were mixed and pulverized to give a wettable powder containing 17.9 % of guazatine trilaurate (6.6% as guazatine).

EXAMPLE 2

Wettable powder:

Ten parts of guazatine triacetate, 13 parts of sodium laurate, 15 parts of white carbon, 5 parts of polyoxyethylene nonylphenyl ether and 57 parts of finely divided clay were mixed and pulverized to give a wettable powder having a guazatine content of 6.6%. Prior to use in an agricultural field, water was added to the wettable powder to perform salt exchanging reaction and give a uniform spray liquid.

EXAMPLE 3

Use at the time of application:

One part of a guazatine triacetate liquid formulation (the same as that produced in Control Example 4) was dissolved in 400 parts of water, and then 0.6 part of a 30% methanol solution of ammonium laurate was added. The mixture was stirred to perform salt exchanging reaction and prepare a uniform spray liquid.

EXAMPLE 4

Wettable powder:

Guazatine sesquicarbonate (8.4 parts) was dissolved in 150 parts of methanol at 50° C., and with stirring, 14.9 parts of laurylsulfuric acid was added. Then, methanol was evaporated under reduced pressure to give 21.6 parts of guazatine trilaurylsulfate (compound No. 9).

Guazatine trilaurylsulfate (21.6 parts), 30 parts of white carbon, 5 parts of polyoxyethylene nonylphenyl ether and 43.4 parts of finely divided clay were mixed and pulverized to give a wettable powder having a guazatine content of 6.6%.

EXAMPLE 5

Wettable powder:

Ten parts of guazatine triacetate, 16.2 parts of sodium laurylsulfate, 15 parts of white carbon, 5 parts of polyoxyethylene nonylphenyl ether and 53.8 parts of finely divided clay to give a wettable powder having a guazatine content of 6.6%. This wettable powder was added to water prior to use in an agricultural field to perform salt exchanging reaction and give a uniform spray liquid.

EXAMPLE 6

Mixing at the time of application:

One part of a guazatine triacetate liquid formulation (the same as that prepared in Control Example 4) was dissolved in 400 parts of water, and then 0.5 part of a 30% methanol solution of sodium laurylsulfate. The mixture was stirred to perform salt exchanging reaction and give a uniform spray liquid.

EXAMPLE 7

Wettable powder:

Guazatine sesquicarbonate (8.4 parts) was dissolved in 150 parts of methanol, and with stirring, 18.3 parts of dodecylbenzenesulfonic acid was added. Then, under reduced pressure, methanol was evaporated to give 24.9 parts of guazatine tridodecylbenzenesulfonate (compound No. 13).

Guazatine tridodecylbenzenesulfonate (24.9 parts), 30 parts of white carbon, 5 parts of polyoxyethylene nonyl phenyl ether and 40.1 parts of finely divided clay were mixed and pulverized to give a wettable powder having a guazatine content of 6.6%.

EXAMPLE 8

Wettable powder:
Ten parts of guazatine triacetate, 20 parts of sodium dodecylbenzenesulfonate, 15 parts of white carbon, 5 parts of polyoxyethylene nonylphenyl ether and 50 parts of finely divided clay were mixed and pulverized to give a wettable powder having a guazatine content of 6.6%. Prior to use in an agricultural field, water was added to the wettable powder, and they were stirred to perform salt exchanging reaction and give a uniform spray liquid.

EXAMPLE 9

Mixing at the time of application:
One part of a guazatine triacetate liquid formulation (the same as that prepared in Control Example 4) was dissolved in 400 parts of water, and then 0.8 part of a 30% methanol solution of sodium dodecylbenzenesulfonate was added. The mixture was stirred to perform salt exchanging reaction and give a uniform spray liquid.

EXAMPLE 10

Emulsifiable concentrate:
Guazatine tridodecylbenzenesulfonate (compound No. 13; 24.9 parts), 1 part of calcium dodecylbenzenesulfonate, 5 parts of polyoxyethylene nonylphenyl ether and 69.1 parts of dimethyl sulfoxide were mixed to form an emulsifiable concentrate having a guazatine content of 6.6%.

EXAMPLE 11

Dust:
Guazatine tridodecylbenzenesulfonate (compound No. 13; 5 parts), 5 parts of white carbon, 30 parts of talc and 60 parts of clay were mixed and pulverized to give a dust having a guazatine content of 1.3%.

EXAMPLE 12

Wettable powder:
Guazatine tripalmitate (21.0 parts) obtained in the same way as in Example 1, 30 parts of white carbon, 5 parts of polyoxyethylene nonylphenyl ether and 44 parts of finely divided clay were mixed and pulverized to give a wettable powder having a guazatine content of 6.6%.

EXAMPLE 13

Wettable powder:
Guazatine tristearate (22.6 parts) obtained in the same way as in Example 1, 30 parts of white carbon, 5 parts of polyoxyethylene nonylphenyl ether and 42.4 parts of finely divided clay were mixed and pulverized to give a wettable powder having a guazatine content of 6.6%.

EXAMPLE 14

Wettable powder:
Guazatine trilinolate (22.3 parts) obtained in the same way as in Example 1, 30 parts of white carbon, 5 parts of polyoxyethylene nonylphenyl ether and 42.7 parts of finely divided clay were mixed and pulverized to give a wettable powder having a guazatine content of 6.6%.

EXAMPLE 15

Wettable powder:
Guazatine triabietate (23.6 parts) obtained in the same way as in Example 1, 30 parts of white carbon, 5 parts of polyoxyethylene nonylphenyl ether and 41.4 parts of finely divided clay were mixed and pulverized to give a wettable powder having a guazatine content of 6.6%.

EXAMPLE 16

Wettable powder:
Guazatine di(2-ethylhexyl) triphosphate (24.7 parts) obtained in the same way as in Example 1, 30 parts of white carbon, 5 parts of polyoxyethylene nonylphenyl ether and 40.3 parts of finely divided clay were mixed and pulverized to give a wettable powder having a guazatine content of 6.6%.

EXAMPLE 17

Wettable powder:
Guazatine tridodecylbenzenesulfonate (compound No. 13; 62.3 parts), 5 parts of dinonylphenyl polyoxyethylene ammonium salt and 32.7 parts of white carbon were mixed and pulverized to give a wettable powder having a guazatine content of 16.6%.

EXAMPLE 18

Wettable powder:
Guazatine triacetate (25 parts), 55 parts of sodium dodecylbenzenesulfonate, 5 parts of dinonylphenyl polyoxyethylene sulfate ammonium salt and 15 parts of white carbon were mixed and pulverized to give a wettable powder having a guazatine content of 16.6%.

EXAMPLE 19

Paste:
Guazatine tridodecylbenzenesulfonate (compound No. 13; 7.5 parts), 1 part of polyoxyethylene nonylphenyl ether and 6 parts of white carbon were mixed and pulverized and 70 parts of a vinyl acetate emulsion resin and 15.5 parts of water were added. They were mixed with stirring to give a paste having a guazatine content of 2.0%.

CONTROL EXAMPLE 1

Wettable powder of guazatine triacetate:
Ten parts of guazatine triacetate, 30 parts of white carbon, 5 parts of polyoxyethylene nonylphenyl ether and 55 parts of finely divided clay were mixed and pulverized to give a wettable powder having a guazatine content of 6.6%.

CONTROL EXAMPLE 2

Wettable powder of guazatine tri-p-toluenesulfonate:
Guazatine tri-p-toluenesulfonate (17.5 parts), 30 parts of white carbon, 5 parts of polyoxyethylene nonylphenyl ether and 47.5 parts of finely divided clay were mixed and pulverized to give a wettable powder having a guazatine content of 6.6%.

CONTROL EXAMPLE 3

Wettable powder of guazatine sesquicarbonate:
Guazatine sesquicarbonate (8.4 parts), 30 parts of white carbon, 5 parts of polyoxyethylene nonylphenyl ether and 56.6 parts of finely divided clay were mixed and pulverized to give a wettable powder having a guazatine content of 6.6%.

CONTROL EXAMPLE 4

Liquid formulation of guazatine triacetate:

Ten parts of guazatine triacetate and 5 parts of polyoxyethylene nonylphenyl ether were dissolved in 85 parts of water to give a liquid formulation having a guazatine content of 6.6%.

CONTROL EXAMPLE 5

Liquid formulation of guazatine triacetate:

Guazatine triacetate (25 parts) and 5 parts of polyoxyethylene secondary alkyl ether were dissolved in 70 parts of water to give a liquid preparation having a guazatine content of 16.6%.

CONTROL EXAMPLE 6

Paste of guazatine triacetate:

Guazatine triacetate (3 parts) and 85 parts of a vinyl acetate emulsion resin were added to 12 parts of water, and the mixture was stirred to give a paste having a guazatine content of 2.0%.

TEST EXAMPLE 1

Phytotoxicity test: Each of the chemicals prepared in Examples 1 to 16 and Control Examples 1 to 4 was sprayed onto the following plants, and 7 days later, the degree of phytotoxicity to the leaves was examined on the following standards. The results are shown in Table 2.

Plants Tested

Rice (*Oryza sativa*; variety "koshihikari") grown in pots with a diameter of 9 cm (in the 3-leaf stage);
turnip (*Brassica campestris*; variety "takane kokabu") grown in pots with a diameter of 12 cm (in the 4-leaf stage);
cucumber (*Cucumis sativus*; variety "shintokiwa") grown in pots with a diameter of 12 cm (in the 2-leaf stage);
soybean (*Glycine max*; variety "enrei") grown in pots with a diameter of 12 cm (in the 2-leaf stage);
rose (variety "landora") grown in Wagner pots (1/5000 a); and
pear (*Pyrus serotina*; variety "kosui") grown in pots with a diameter of 30 cm (4 years old).

Standards of Phytotoxicity

The degree of phytotoxity was rated on a scale of 0 to 5 as follows:

| Phytotoxity rating | Degree of phytotoxicity |
|---|---|
| 5 | Heavy |
| 4 | Great |
| 3 | Medium |
| 2 | Small |
| 1 | Slight |
| 0 | None |

TABLE 2

| Chemical | Dilution ratio | Rice | Turnip | Cucumber | Soybean | Rose | Pear |
|---|---|---|---|---|---|---|---|
| Example | | | | | | | |
| 1 | 400 | 0 | 1 | 2 | 2 | 2 | 2 |
| 2 | " | 0 | 1 | 2 | 2 | 2 | 2 |
| 3 | No dilution | 0 | 1 | 2 | 2 | 2 | 2 |
| 4 | 400 | 0 | 0 | 1 | 1 | 1 | 1 |
| 5 | " | 0 | 0 | 1 | 1 | 1 | 1 |
| 6 | No dilution | 0 | 0 | 1 | 1 | 1 | 1 |
| 7 | 400 | 0 | 0 | 0 | 0 | 0 | 0 |
| 8 | " | 0 | 0 | 0 | 0 | 0 | 0 |
| 9 | No dilution | 0 | 0 | 0 | 1 | 1 | 0 |
| 10 | 400 | 0 | 0 | 1 | 2 | 1 | 1 |
| 11 | — | 0 | — | — | 0 | — | — |
| 12 | 400 | 0 | 1 | 2 | 2 | 2 | 2 |
| 13 | " | 0 | 1 | 2 | 2 | 2 | 2 |
| 14 | " | 0 | 0 | 1 | 2 | 2 | 1 |
| 15 | " | 0 | 0 | 1 | 1 | 1 | 1 |
| 16 | " | 0 | 0 | 1 | 0 | 1 | 1 |
| Control Example | | | | | | | |
| 1 | 400 | 3 | 2 | 4 | 5 | 4 | 5 |
| 2 | " | 3 | 2 | 4 | 5 | 4 | 5 |
| 3 | " | 3 | 2 | 4 | 5 | 4 | 5 |
| 4 | " | 3 | 2 | 4 | 5 | 4 | 5 |

TEST EXAMPLE 2

Control test on brown spot of rice (*Cochliobolus miyabeanus*):

Each of the chemicals prepared in Examples 1 to 11 and Control Examples 1 to 4 was sprayed onto rice seedlings in the 3- to 4-leaf stage grown in pots having a diameter of 9 cm, and then dried on standing. The rice seedlings were inoculated with a suspension of *Cochliobolus miyabeanus* by spraying. Seven days after the inoculation, the number of lesions in a leaf which was youngest at the time of spraying was counted, and the protective value was calculated in accordance with the following equation. The results are shown in Table 3.

$$\text{Protective value (\%)} = \left(1 - \frac{\text{Number of lesions per leaf in the sprayed plants}}{\text{Number of lesions per leaf in the non-sprayed plants}}\right) \times 100$$

The phytotoxicity of the chemicals was also evaluated by the same phytotoxicity rating as in Test Example 1.

TABLE 3

| Chemical | Dilution ratio | Protective value (%) | Phytotoxicity rating |
|---|---|---|---|
| Example | | | |
| 1 | 800 | 93.3 | 0 |
| 2 | " | 93.0 | 0 |
| 3 | 2 | 94.3 | 0 |
| 4 | 800 | 91.0 | 0 |
| 5 | " | 94.7 | 0 |
| 6 | 2 | 94.6 | 0 |
| 7 | 800 | 91.1 | 0 |
| 8 | " | 96.4 | 0 |
| 9 | 2 | 90.6 | 0 |
| 10 | 800 | 87.8 | 0 |
| 11 | — | 89.3 | 0 |
| Control Example | | | |
| 1 | 800 | 92.0 | 3 |
| 2 | " | 93.4 | 3 |
| 3 | " | 95.4 | 3 |
| 4 | " | 88.6 | 3 |

The results given in Table 3 show that the fungicides of this invention have an equivalent control effect to conventional guanidine-type fungicides and had reduced phytotoxicity.

TEST EXAMPLE 3

Phytotoxity test on fruit trees:

Test Plants

Pear (variety: "kosui" and "chojuro"),
peach (variety: "hakuto"),
cherry (variety: "napoleon"),
plum (variety: "shirokaga"),
chestnut (variety: "tanzawa"),
persimmon (variety: "fuyu"),
grape (variety: "kyoho" and "neomuscat"), and
mandarine orange (variety: "unshu").

Period of Application

Applied five times at intervals of 10 to 14 days during May to July.

Chemicals and Evaluation

Each of the chemicals obtained in Examples 17 and 18 and Control Example 5 was sprayed onto each of the above fruit trees. Seven days after the day of final spraying, the presence or absence of phytotoxicity to the leaves and fruits was tested as in Test Example 1. The results are shown in Table 4.

also evaluated by the following rating. The results are shown in Table 5.

Rating of evaluating callus formation:
0: No formation of a callus
1: callus formed in 20% of the peeled portion
2: callus formed in 40% of the peeled portion
3: callus formed in 60% of the peeled portion
4: callus formed in 80% of the peeled portion
5: callus formed in 100% of the peeled portion

TABLE 5

| Chemical | Phytotoxicity rating | | | Callus formation rating | | |
|---|---|---|---|---|---|---|
| | Pear | Peach | Apple | Pear | Peach | Apple |
| Example 19 | 0 | 0 | 0 | 5 | 5 | 5 |
| Control Example 6 | 4 | 4 | 2 | 1 | 3 | 2 |
| Non-treated | 0 | 0 | 0 | 5 | 5 | 5 |

The results given in Table 5 show the reduced phytotoxicity of the fungicide of this invention.

TEST EXAMPLE 5

Phytotoxicity test:

Each of the chemicals obtained in Examples 17 and 18 was sprayed six times at intervals of 7 days onto each of the following plants, and 7 days after the day of the final spraying, the degree of phytotoxicity was examined in the same way as in Test Example 1. The results are shown in Table 6.

TABLE 4

| Chemicals | Dilution ratio | Phytotoxicity rating | | | | | | | | |
|---|---|---|---|---|---|---|---|---|---|---|
| | | pear | | peach | cherry | plum | chestnut | persimmon | grape | | mandarine orange |
| | | kosui | chojuro | hakuto | napoleon | shiro-kaga | tanzawa | fuyu | kyoho | neo-muscat | unshu |
| Example 17 | 500 | 0 | 0 | 1 | 0 | 0 | 0 | 1 | 0 | 0 | 0 |
| | 1000 | 0 | 0 | 0 | 0 | 0 | 0 | 0 | 0 | 0 | 0 |
| | 2000 | 0 | 0 | 0 | 0 | — | — | — | — | — | — |
| Example 18 | 70 | 1 | 0 | 2 | 1 | 0 | 0 | 1 | 1 | 0 | 0 |
| | 1000 | 0 | 0 | 0 | 1 | 0 | 0 | 1 | 0 | 0 | 0 |
| | 2000 | 0 | 0 | 0 | 0 | — | — | — | — | — | — |
| Control Example 5 | 500 | 5 | 3 | 4 | 3 | 2 | 4 | 5 | 2 | 2 | 1 |
| | 1000 | 3 | 2 | 4 | 2 | 1 | 3 | 3 | 1 | 1 | 0 |
| | 2000 | 2 | 1 | 2 | 1 | — | — | — | — | — | — |

Note: The mark "—" shows that the test was not conducted.

The results of Table 4 demonstrate the reduced phytotoxicity of the fungicides of this invention.

TEST EXAMPLE 4

Phytotoxicity test on fruit trees:

Test Plants

Pear (variety: "shinsui")
peach (variety "Ohkubo")
apple (variety: "starking")

Method of examination

In May, the bark was peeled off in a size of 2×6 cm at two sites on the trunk of each of the above trees, and each of the pastes obtained in Example 19 and Control Example 6 was coated on the peeled portions. For comparison, the results obtained in the absence of treatment with the past are also shown.

Method of Evaluation

Sixth months after coating, the degree of phytotoxicity in the coated portions was evaluated by the same rating as in Example 1 and the formation of callus was

Test Plants

Watermelon (variety: "shimatama"),
melon (variety: "prince melon"),
eggplant (variety: "senryo No. 2"),
tomato (variety: "raiden"),
radish (variety: "tokinashi"),
rose (variety: "landora"), and
rice (variety: "koshihikari").

TABLE 6

| Chemical | Dilution ratio | Phytotoxicity rating | | | | | | |
|---|---|---|---|---|---|---|---|---|
| | | Watermelon | melon | eggplant | tomato | radish | rose | rice |
| Example 17 | 500 | 0 | 0 | 0 | 0 | 0 | 1 | 0 |
| | 1000 | 0 | 0 | 0 | 0 | 0 | 0 | 0 |
| Example 18 | 500 | 0 | 1 | 0 | 0 | 0 | 1 | 1 |
| | 1000 | 0 | 0 | 0 | 0 | 0 | 0 | 0 |
| Control Example 5 | 500 | 3 | 4 | 2 | 2 | 3 | 4 | 3 |
| | 1000 | 2 | 3 | 0 | 0 | 2 | 3 | 2 |

The results given in Table 6 demonstrate the reduced phytotoxicity of the fungicides of this invention.

TEST EXAMPLE 6

Efficacy on pear scab (*Venturia nashicola*) and phytotoxicity to pear;

Each of the chemical obtained in Example 17 and a polycarbamate wettable powder was sprayed 7 times at intervals of 10 days onto pear trees (variety: "hosui") (three trees for each active ingredient concentration) during May to July. Seven days after the final spraying, the ratio of infected leaves and the degree of phytotoxicity were investigated on 200 leaves in each tree. The results are shown in Table 7. The results of Table 7 demonstrate the superior efficacy, and the freedom from phytotoxicity, of the fungicide of this invention.

TABLE 7

| Chemical | Dilution ratio | Concentration of the active ingredient (ppm) | Ratio of infected leaves (%) | Phytotoxicity |
|---|---|---|---|---|
| Example 17 | 1000 | 600 | 0.4 | None |
|  | 1000 | 300 | 1.8 | None |
| Polycarbamate wettable powder | 800 | 1000 | 3.4 | None |
| Not sprayed | — | — | 22.1 | — |

TEST EXAMPLE 7

Efficacy on peach brown rot (*Sclerotinia cinerea*) and phytotoxicity to peach;

Each of the chemical obtained in Example 17 and a benomyl wettable powder was sprayed four times at intervals of 10 days in June to July onto peach (variety: "kurakata wase") (one tree for each area). Seven days after the final spraying, 10 fruits were harvested from each area, and a spore suspension of *Sclerotinia cinerea* was inoculated in five parts of every fruit. Five days later, the ratio of infected fruits was investigated. The results are shown in Table 8. The results of Table 8 demonstrate the superior efficacy, and the freedom from phytotoxicity, of the fungicide of this invention.

TABLE 8

| Chemical | Dilution ratio | Concentration of the active ingredient (ppm) | Ratio of infected fruits (%) | Phytotoxicity |
|---|---|---|---|---|
| Example 17 | 2000 | 300 | 9 | None |
| Benomyl wettable powder | 2000 | 250 | 18 | None |
| Not sprayed | — | — | 92 | — |

TEST EXAMPLE 8

Efficacy on apple leaf spot (*Alternaria mali*) and phytotoxicity to apple:

Each of the chemical obtained in Example 18 and an oxine-copper wettable powder was sprayed six times at intervals of 10 days onto trees of apple (variety: "starking") (10 trees for each active ingredient concentration) during July to August. Fourteen days after the final spraying, 60 shoots were randomly selected from each concentration group, and the ratio of infected leaves was investigated on all of the leaves of these shoots. The results are shown in Table 9. The results of Table 9 demonstrate the superior efficacy, and the freedom from phytotoxicity, of the fungicide of this invention.

TABLE 9

| Chemical | Dilution ratio | Concentration of the active ingredient (ppm) | Ratio of infected leaves (%) | Phytotoxicity |
|---|---|---|---|---|
| Example 18 | 1000 | 600 | 11.8 | None |
|  | 1500 | 400 | 14.4 | None |
| Oxine-copper wettable powder | 600 | 667 | 21.1 | None |
| Non-treated | — | — | 98.5 | — |

What is claimed is:

1. An agricultural and horticultural guanidinetype fungicide of low phytotoxicity comprising as an active ingredient an addition salt between a fungicidal guanidine compound and an acid having an oleophilic group with 9 to 25 carbon atoms in total, said fungicidal guanidine compound being at least one compound selected from the group consisting of 1,1'-iminodi(octamethylene)diguanidine, 1,8-diguanidinooctane, 1,12-diguanidinododecane, bis(8-guanidinooctyl)ether, bis(8-guanidinooctyl)thioether, 8-guanidinooctyl-3-guanidinopropyl ether and aliphatic polyamines having a guanidino group introduced thereinto, said acid having an oleophilic group being at least one acid selected from the group consisting of a sulfuric acid monoester, a sulfonic acid, a phosphoric acid monoester and a phosphoric acid diester.

2. The fungicide of claim 1 wherein the acid having an oleophilic group is a sulfonic acid having an oleophilic group with from 9 to 25 carbon atoms and selected from the group consisting of primary alkyl sulfonic acids, secondary alkyl sulfonic acids, sulfonic acids of fatty acid esters, sulfonic acids of alkyl ethers, alkyl sulfonic acids of fatty acid amides, sulfosuccinic acid esters, alkyl benzene sulfonic acids in which the alkyl moiety has from 8 to 14 carbon atoms, alkyl phenyl sulfonic acids, alkyl naphthalene sulfonic acids, alkyl diphenyl sulfonic acids, alkylaryl ether sulfonic acids, alkylaryl ester sulfonic acids, alkylaryl ketone sulfonic acids, alkyl benzomidazole sulfonic acids, lignin sulfonic acids and mixtures of 2 or more thereof.

3. The fungicide of claim 2 wherein the sulfonic acid is an alkyl benzene sulfonic acid selected from the group consisting of dodecyl benzene sulfonic acid, and tridecyl sulfonic acid.

4. The fungicide of claim 3 wherein the fungicidal guanidine compound is 1,1'-amino di(octamethylene) diguanidine.

5. The fungicide of claim 1 wherein the fungicidal guanidine compound is 1,1'amino di(octamethylene) diguanidine.

6. An agricultural and horticultural fungicidal composition of low phytotoxicity which comprises a fungicidally effective amount of the low phytotoxic fungicide of claim 9 in admixture with a liquid or solid carrier.

7. A method for protecting agricultural and horticultural plants from the effects of plant disease causing fungi which comprises applying to the plants or to the soil in which the plants grow a fungicidally effective amount of the low phytotoxic fungicide of claim 1.

8. The method of claim 7 wherein the fungicide is the acid addition salt of 1,1'-amino di(octamethylene) diguanidine with dodecyl benzene sulfonate or tridecyl benzene sulfonate.

* * * * *

UNITED STATES PATENT AND TRADEMARK OFFICE
CERTIFICATE OF CORRECTION

PATENT NO. : 4,659,739
DATED : April 21, 1987
INVENTOR(S) : NOBUYUKI YOSHIOKA, ET AL.

It is certified that error appears in the above-identified patent and that said Letters Patent is hereby corrected as shown below:

IN THE CLAIMS

Column 14, line 57, claim 6, delete "9", insert --1--.

Signed and Sealed this

Twenty-ninth Day of September, 1987

Attest:

DONALD J. QUIGG

Attesting Officer      Commissioner of Patents and Trademarks